US00PP13494P2

(12) United States Plant Patent
Slaughter et al.

(10) Patent No.: US PP13,494 P2
(45) Date of Patent: Jan. 21, 2003

(54) PEACH TREE NAMED 'BURPEACHNINE'

(75) Inventors: John K. Slaughter, Clovis, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 10/014,309

(22) Filed: Dec. 11, 2001

(51) Int. Cl.[7] ..... A01H 5/00

(52) U.S. Cl. ..... Plt./197

(58) Field of Search ..... Plt./197

*Primary Examiner*—Bruce R. Campell
*Assistant Examiner*—Susan B. McCormick
(74) *Attorney, Agent, or Firm*—Wells St. John P.S.

(57) ABSTRACT

A new and distinct variety of peach tree (*Prunus persica*), denominated varietally as 'Burpeachnine', and which is characterized as to novelty by producing an attractively colored yellow-fleshed clingstone peach which is mature for harvesting and shipment approximately June 8 to June 18 under the ecological conditions prevailing in the San Joaquin Valley of Central California.

1 Drawing Sheet

BOTANICAL CLASSIFICATION

*Prunus persica.*

VARIETY DENOMINATION

'BURPEACHNINE'.

BACKGROUND OF THE NEW VARIETY

The present invention relates to a new, novel and distinct variety of peach tree, *Prunus persica,* which has been denominated varietally as 'Burpeachnine'. The present variety of peach tree resulted from an on-going program of fruit and nut tree breeding. The purpose of this program is to improve the commercial quality of deciduous fruit and nut tree varieties and rootstocks by creating and releasing promising selections of prunus, malus and regia species. To this end we make both controlled and hybrid cross pollinations each year in order to produce seedling populations from which improved progenies are evaluated and selected.

The seedling 'Burpeachnine' was originated by us from a population of seedlings grown in our experimental orchards located near Fowler, Calif. The seedlings, grown on their own roots, were the result of a controlled cross of the peach tree 'Rich Lady' (U.S. Plant Pat. No. 7,290) used as the seed parent, and the nectarine tree 'Mayfire' (unpatented) which was used as the pollen parent. One seedling, that is, the present variety, exhibited especially desirable characteristics and was marked for subsequent observation. After the 1997 season, the new, present variety, was selected for advanced evaluation and repropagation.

ASEXUAL REPRODUCTION

Asexual reproduction of the new and distinct variety of peach tree was accomplished by budding to 'Nemaguard' Rootstock (non-patented). This was performed by us in our experimental orchard located near Fowler, Calif. Subsequent evaluations have shown those reproductions run true to the original tree. All characteristics of the original tree and its fruit were established and appeared to be transmitted through succeeding asexual propagations.

SUMMARY OF THE VARIETY

'Burpeachnine' is a new and distinct variety of peach tree, which is of medium to large size, has vigorous growth, and is a regular and productive bearer of large, firm yellow flesh, semi-freestone fruit with good flavor and eating quality. The tree has a medium chilling requirement of approximately 550 hours. The tree also produces relatively uniformly sized fruit, throughout the tree with a high degree of red skin coloration, and firm flesh. The fruit appears to have good handling and shipping quality. The 'Burpeachnine' peach tree bears fruit that is ripe for commercial harvesting and shipment on approximately June 8 to June 18 under the ecological conditions prevailing in central California. In comparison to the parent 'Rich Lady' Peach tree (U.S. Plant Pat. No. 7,290), the new variety ripens about 10 or more days earlier.

BRIEF DESCRIPTION OF THE DRAWING

The drawing provided is of the present variety and consists of two separate images. The upper image is a lateral view of three whole fruits placed on a centimeter grid. All of these fruits are placed apex up and are displayed at shipping ripe maturity. The lower image consists of four pieces of fruit, a typical leaf shoot and an extracted pit that has had the flesh removed and is lying on its lateral side. Three of the fruits in this image are whole and are lying on their basal, apical and suture sides respectively. The fourth fruit has been bisected along the equatorial plane and displays an apical view of the fruit, flesh and pit intact. Due to chemical development, processing and printing of the photographic image, the leaves, pit and fruit depicted in this photograph may or may not be accurate when compared to the actual botanical specimens. For this reason, future color references should be made to the color plates (Royal Horticultural Society) and the descriptions provided hereinafter.

DETAILED DESCRIPTION

Referring more specifically to the pomological details of this new and distinct variety of peach tree, the following has been observed during the fifth fruiting season under the ecological conditions prevailing at the orchards located near the town of Fowler, county of Fresno, state of California. All major color code designations are by reference to The R.H.S. Colour Chart (Fourth Edition) provided by The Royal Horticultural Society of Great Britain.

Tree:

*Size.*—Generally. — Considered as medium compared to other common commercial peach cultivars ripening in the mid season of maturity. The tree was pruned to a height of 304.8 cm to 365.7 cm at maturity.

*Vigor.*—Moderately vigorous. The variety grew from about 121.92 cm to 182.8 cm in height the first growing season. The variety was pruned to a height of 106.7 cm during the first dormant season and primary scaffolds were then selected for the desired tree structure.

*Productivity.*—Productive. Fruit set varies from about 1.5 to several times more than the desired crop load. Fruit set is spaced by thinning to develop into the desired market sized fruit. The number of the fruit set varies with climatic conditions and cultural practices during the bloom period.

*Bearer.*—Regular. Fruit set has been heavy and thinning has been necessary the past 4 years.

*Form.*—Upright, and pruned to a vase shape.

*Density.*—Medium dense. It has been discovered that pruning the branches from the center of the tree to obtain a vase shape allows for air movement and sunlight to enhance fruit color and renewal of fruiting wood throughout the tree.

*Hardiness.*—The present tree was grown and evaluated in USDA Hardiness Zone 9. Winter chilling requirements were determined to be approximately 550 hours at or below 7.0 degrees C. The variety was considered hardy under typical Central San Joaquin Valley conditions.

Trunk:

*Diameter.*—Approximately 14.0 cm in diameter when measured at a distance of approximately 15.24 cm above the soil level, at the end of the fourth growing season.

*Bark texture.*—Considered moderately rough with numerous folds of papery scarfskin being present.

*Lenticels.*—Numerous flat, oval lenticels are present. The lenticels range in size from approximately 2.0 to about 6.0 millimeters in width, and from 1 to 2 millimeters in height.

*Lenticel color.*—Considered an Orange Brown. (RHS Greyed-Orange Group N172 A). Bark Coloration. — Variable, but it is generally considered to be a grey-brown (RHS Greyed-Orange Group 177 A).

Branches:

*Size.*—Considered medium for the variety.

*Diameter.*—Average as compared to other varieties. The branches have a diameter of about 70.0 millimeters when measured during the third year after grafting.

*Surface texture.*—Average, and appearing furrowed on wood which is several years old.

*Crotch angles.*—Primary branches considered variable between about 44 to 49 degrees from the horizontal axis. This characteristic is not distinctive of the variety however.

*Current season shoots.*—Surface texture — Substantially glabrous.

*Internode length.*—Approximately 2.0 to 2.2 cm.

*Color of mature branches.*—Medium brown, (RHS Grey Orange Group N199C).

*Current seasons shoots.*—Color. — Light green, (RHS Yellow Green Group 144 D). The color of new shoot tips is considered a bright and shiny green (RHS Green Group 134 C).

Leaves:

*Size.*—Considered medium for the species. Leaf measurements have been taken from vigorous upright current season growth taken approximately at mid-shoot.

*Leaf length.*—Approximately 140 to 170 millimeters.

*Leaf width.*—Approximately 32 to 35 millimeters.

*Leaf base shape.*—Slightly oblique relative to the leaf longitudinal axis.

*Leaf form.*—Lanceolate.

*Leaf tip form.*—Acuminate.

*Leaf color.*—Dark green, (RHS Green Group N138 B).

*Leaf texture.*—Glabrous.

*Lower surface.*—Medium green, (RHS Yellow-Green Group 148 A).

*Leaf venation.*—Pinnately veined.

*Mid-vein.*—Color. — Light yellow green, (RHS Yellow Green Group 151 A).

*Leaf margins.*—Slightly undulating. Form. — Considered crenate, occasionally doubly crenate. Uniformity. — Considered generally uniform.

*Leaf petioles.*—Size. — Considered medium long to long. Length. — approximately 9.0 to about 12.0 mm. Diameter. — about 1.5 to about 2.5 mm. Color. — Pale green, (RHS Yellow Green Group 151 A).

*Leaf glands.*—Size. — about 1.0 mm in height and about 1.0 to about 2.0 mm in width. Numbers. — Generally one per side, occasionally two per side. Type. — Reniform, considered reasonably unappressed to the petiole margin. Color. — Greenish brown (RHS Yellow Green Group152 B).

*Leaf stipules.*—Size. — Medium large for the variety. Number. — Typically 2 per leaf bud and up to 6 per shoot tip. Form. — Lanceolate in form and having a serrated margin. Color. — Green, (RHS Green Group 132 A) when young but graduating to a yellow-brown color (RHS Grey Orange group 177 A) with advancing senescence. The stipules are considered to be early deciduous.

Flowers:

*Flower buds.*—Generally — The floral buds are considered to be large, about 15 millimeters wide, and about 21 millimeters long, in size; conic in form; and slightly appressed relative to the bearing shoot.

*Flower buds.*—Color — The bud scales are gray-brown, (approximately RHS Greyed Purple Group 183 A). The buds are considered hardy under typical central San Joaquin Valley climatic conditions.

*Hardiness.*—No winter injury has been noted during the last several years of evaluation in The Central San Joaquin Valley. The current variety has not been intentionally subjected to drought or heat stress and therefore this information is not available.

*Date of first bloom.*—Feb. 19, 1999.

*Blooming time.*—Considered early in relative comparison to other commercial peach cultivars commonly grown in the central San Joaquin valley. Date of full bloom was observed on Feb. 25, 1999. The date of bloom varies slightly with climatic conditions.

*Duration of bloom.*—Approximately 9 days.

*Flower type.*—The present variety is considered to have a showy type flower.

*Flower size.*—Flower diameter at full bloom is approximately 31.0 to 36.0 millimeters.

*Bloom quantity.*—Considered abundant.

*Flower bud frequency.*—Normally 1 to 2 appear per node.

*Petal size.*—Generally — Considered medium large to large for the species. Length. — Approximately 16.0 to 19.0 millimeters. Width. — Approximately 18.0 to 20.0 millimeters.

*Petal form.*—Broadly ovate.

*Petal count.*—Nearly always 5.

*Petal texture.*—Glabrous.

*Petal color.*—Light pink when young, (RHS Red Purple Group 63 C), and darkening with advancing senescence and exposure to sunlight to a medium to dark pink (RHS Red Purple Group 64 D).

*Fragrance.*—Slight.

*Petal claw.*—Form. — The claw is considered truncate, and has a medium-large size when compared to other varieties. Length. — Approximately 8.0 to 10.0 millimeters. Width. — Approximately 6.0 to 8.0 millimeters.

*Petal margins.*—Generally considered variable, from nearly smooth, to moderately undulate and ruffled, especially apically.

*Petal apex.*—Generally — The petal apices appear slightly domed.

*Flower pedicel.*—Length. — Considered medium-long, and having an average length of approximately 3.0 to 5.0 millimeters. Diameter. — Considered average, approximately 2.0 millimeters. Color. — A medium Green (RHS Grey Brown Group N199 D).

*Floral nectaries.*—Color. — A dull orange-gold (RHS Greyed Orange Group 172 B).

*Calyx.*—Surface Texture. — Generally glabrous. Color. — A dull red, (approximately RHS Greyed Purple Group 183 A).

*Sepals.*—Surface Texture. — The surface has a short, fine, wooly and a gray colored texture. Size. — Average, and ovate in form. Color. — A dull red, (approximately RHS Greyed-Red Group 178 A).

*Anthers.*—Generally. — Average to above average in length. Color. — Red to reddish-orange dorsally (approximately RHS Greyed Purple Group 179 A).

*Pollen production.*—Pollen is abundant, and has a yellow color, (approximately RHS Yellow Orange Group 17 B).

*Filaments.*—Size. — Variable in length, approximately 11.0 to about 13.0 millimeters in length. Color. — White, (RHS Red Purple Group 62 D).

*Pistil.*—Number. — Usually 1, rarely 2. Generally. — Average in size. Length. — Approximately 14.0 to about 16.0 millimeters including the ovary. Color. — Considered a very pale green, (approximately RHS Yellow Green Group 151 D). Surface Texture. — The variety has a long, pale green to whitish-yellow pubescent pistil.

Fruit:

*Maturity when described.*—Firm ripe condition (shipping ripe). Date of first picking. — Jun. 8, 1999. Date of last picking — Jun. 18, 1999. The date of harvesting varies slightly with climatic conditions.

*Size.*—Generally — Medium large, and considered uniform.

*Average cheek diameter.*—Approximately 73.0 to about 75.0 millimeters.

*Average axial diameter.*—Approximately 71.0 to about 73.0 millimeters.

*Typical weight.*—Approximately 231.0 grams. This is highly dependent on cultural practices and is therefore not distinctive of the variety.

*Fruit form.*—Generally — Moderately oblate. The fruit is generally uniform in symmetry.

*Fruit suture.*—Shallow, slightly lipped, and extends from the base to the apex. No apparent callousing or stitching exists along the suture line.

*Suture.*—Color — This appears to be a yellow to golden yellow background, (approximately RHS Yellow Orange Group 22 B) and further having some red orange color (approximately RHS Red Group 45 A).

*Ventral surface.*—Form — Slightly indented.

*Apex.*—Varies from rounded to having a slight apical point.

*Base.*—Obtuse.

*Stem cavity.*—Rounded to slightly elongated in the suture plane. Average depth of the stem cavity is about 1.25 cm. Average width is about 2.51 cm.

*Fruit skin.*—Thickness. — Considered medium in thickness, and tenacious to the flesh. Texture. — Medium, and having a slight pubescence. Taste. — Non-astringent. Tendency to crack. — Not observed.

*Color.*—Blush Color. — This red blush color is variable from a dark red, (approximately RHS Red Group 46 A to 45 B). Ground Color. — Pale yellow white (approximately RHS Yellow 11 B).

*Fruit stem.*—Medium in length, approximately 8.0 to about 9.0 millimeters. Diameter. — Approximately 2.0 to about 3.0 millimeters. Color. — Pale yellow-green (approximately RHS Yellow Green Group 145 B).

*Flesh.*—Ripens. — Evenly. Texture. — Firm, and dense. Fibers. — Few, small, and tender. Aroma. — Very slight. Eating Quality. — Good. Flavor. — Considered sweet and mildly acidic. The flavor is considered both pleasant and balanced. Juice. — Moderate. Brix. — 11.5 degrees. Varies slightly with the number of fruit per tree, cultural and climatic conditions. Flesh Color — Pale yellow, (approximately RHS Yellow Group 10 A).

Stone:

*Type.*—Clingstone.

*Size.*—Considered medium for the variety.

*Length.*—Average about 22.0 to about 24.0 millimeters.

*Width.*—Average about 21.0 to about 22.0 millimeters.

*Diameter.*—Average about 18.0 to about 19.0 millimeters.

*Form.*—Obovoid.

*Base.*—The stone is usually rounded, and varies from rounded to straight.

*Apex.*—Shape.— The stone apex is raised and has an acute, short tip.

*Stone surface.*—Surface Texture — Irregularly furrowed toward the apex, and pitted toward the base. The stone exhibits substantial pitting laterally. Substantial grooving over the apical shoulders is evident. Surface pitting is prominent generally, and more frequently, it is present basally. One long furrow on each side of the suture will be found. Ridges. — The surface texture varies from sharp to rounded. Ventral Edge. — Width — Considered medium, and having a dimension of approximately 5 to about 6.5 millimeters at the mid-suture. The wings are most prominent over the basal area. Dorsal Edge. — Shape. — Full, heavily grooved, and having jagged edges. The dorsal edge is moderately eroded over the apical shoulder.

*Stone color*.—The color of the dry stone is a light to medium brown, (approximately RHS Orange Red Group 34 C).

*Tendency to split*.—Few but very infrequent splitting are noted.

*Kernel*.—Size. — Length 18.0 mm.; Width — 12.0 mm.; Thickness — 3.0 millimeters. Form. — Obovoid. Pellicle. — Pubescent. Color. — (RHS Grey Brown Group N199 C).

*Use*.—The subject variety 'Burpeachnine' is considered to be a Peach tree of mid-season maturity, and which produces fruit which are very firm, attractively colored, and which are useful for both local and long distance shipping.

*Keeping quality*.—Excellent. Fruit has stored well up to 21 days after harvest at 1.0 degree Celsius.

*Shipping quality*.—Good. Fruit showed minimal bruising of flesh or skin damage after normal harvest and packing procedures.

*Resistance to insects and disease*.—No particular susceptibilities were noted, nor has the present variety been subjected to regimes of testing for susceptibilities or resistances to plant and or fruit diseases.

Although the new variety of peach tree possesses the described characteristics when grown under the ecological conditions prevailing near Fowler, Calif., in the Central part of the San Joaquin Valley of California, it will be understood that variations of the usual magnitude and characteristics incident to changes in growing conditions, fertilization, pruning, pest control and horticultural management are to be expected.

Having thus described and illustrated our new variety peach tree, what we claim is new and desire to secure by Plant Letters Patent is:

1. A new distinct variety of peach tree substantially as illustrated and described and which is characterized principally as novelty by producing an attractively colored yellow-fleshed clingstone peach which is mature for harvesting and shipment approximately June 8 to June 18 under the ecological conditions prevailing in the San Joaquin Valley of Central California.

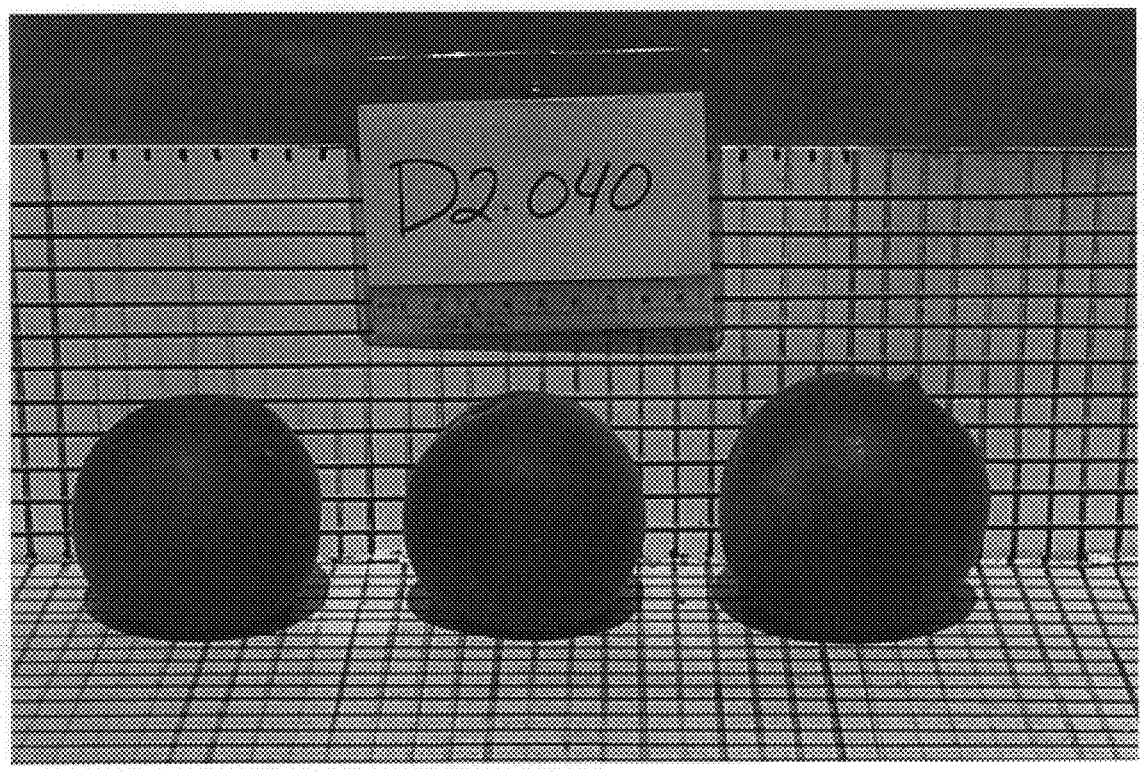
D2.040
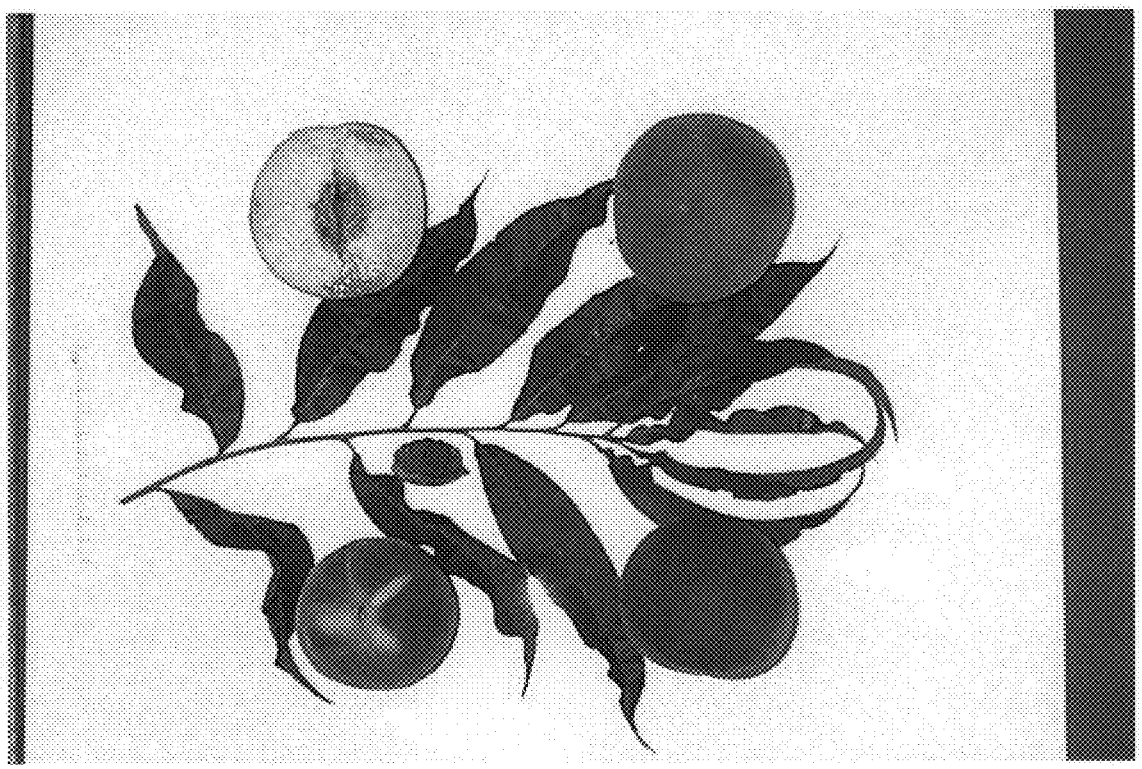

* * * * *